(12) United States Patent
Madsen

(10) Patent No.: US 7,652,176 B2
(45) Date of Patent: Jan. 26, 2010

(54) PROCESS FOR THE PREPARATION OF DIMETHYL ETHER

(75) Inventor: Jørgen Madsen, Hillerød (DK)

(73) Assignee: Haldor Topsøe A/S, Lyngby (DK)

( * ) Notice: Subject to any disclaimer, the term of this patent is extended or adjusted under 35 U.S.C. 154(b) by 0 days.

(21) Appl. No.: 12/188,882

(22) Filed: Aug. 8, 2008

(65) Prior Publication Data

US 2009/0054539 A1   Feb. 26, 2009

(30) Foreign Application Priority Data

Aug. 23, 2007   (DK) ............................ 2007 01204

(51) Int. Cl.
C07C 43/00 (2006.01)
C07C 27/00 (2006.01)

(52) U.S. Cl. ................ 568/698; 518/711; 518/722; 518/724

(58) Field of Classification Search .......... 568/698; 518/711, 722, 724
See application file for complete search history.

(56) References Cited

U.S. PATENT DOCUMENTS 5,908,963 A * 6/1999 Voss et al. ............... 568/671
6,458,856 B1 * 10/2002 Peng et al. ................ 518/700
6,924,399 B2 * 8/2005 Iijima et al. .............. 568/698
7,202,387 B2 * 4/2007 Shoji et al. ................ 568/698

FOREIGN PATENT DOCUMENTS

EP   0 483 609 A1   5/1992

OTHER PUBLICATIONS

E. Riegel et al., "Synthetic Nitrogen Products", Riegel's Handbook of Industrial Chemistry, vol. 10th ed., Jan. 1, 2003, pp. 1177-1184.

* cited by examiner

Primary Examiner—Porfirio Nazario Gonzalez
(74) Attorney, Agent, or Firm—Dickstein Shapiro LLP

(57) ABSTRACT

Process for the preparation of dimethyl ether product by catalytic conversion of synthesis gas to dimethyl ether comprising contacting a stream of synthesis gas comprising carbon dioxide with one or more catalysts active in the formation of methanol and the dehydration of methanol to dimethyl ether to form a product mixture comprising the components dimethyl ether, methanol, carbon dioxide and unconverted synthesis gas, washing the product mixture comprising carbon dioxide and unconverted synthesis gas in a scrubbing zone with a liquid solvent being rich in potassium carbonate or amine and thereby selectively absorbing carbon dioxide in the liquid solvent, subjecting the thus treated product mixture to a distillation step to separate methanol and water from dimethyl ether and unconverted synthesis gas stream with a reduced content of carbon dioxide and separating the unconverted synthesis gas from the dimethyl ether product.

6 Claims, 1 Drawing Sheet

PROCESS FOR THE PREPARATION OF DIMETHYL ETHER

The invention concerns a process for preparation of dimethyl ether from synthesis gas. In particular, the invention concerns an improved dimethyl ether synthesis process by utilising chemical wash of raw product effluent from the ether synthesis step for the removal of carbon dioxide from the raw product to improve process yield and the final purification of produced dimethyl ether.

BACKGROUND OF THE INVENTION

The process of the invention concerns purification of dimethyl ether being produced from carbon oxides and hydrogen containing synthesis gas.

The conversion of synthesis gas to dimethyl ether is carried out in one or more reactors, in which synthesis gas is catalytically converted to methanol shown in equation (1) and dimethyl ether as shown in equation (2). The shift reaction also takes place and is shown in equation (3).

$$CO + 2H_2 \rightarrow CH_3OH \quad (1)$$

$$2CH_3OH \rightarrow CH_3OCH_3 + H_2O \quad (2)$$

$$CO + H_2O \rightarrow CO_2 + H_2 \quad (3)$$

Maximum conversion of synthesis gas is obtained when dimethyl ether is prepared at a stoichiometric ratio between hydrogen and carbon monoxide equal to one. At ratios above or below one less dimethyl ether is prepared. At maximum conversion ($H_2/CO \approx 1$) the overall reaction takes place essentially according to equation (4):

$$3H_2 + 3CO \rightarrow CH_3OCH3 + CO_2 \quad (4)$$

Carbon dioxide is soluble in dimethyl ether, and in order to obtain the dimethyl ether product with a required purity it is necessary to remove the carbon dioxide formed. Additionally, when carbon dioxide is removed the composition of the unconverted synthesis gas, which is recycled to the dimethyl ether synthesis reactor, is close to that of the make up synthesis gas used to prepare dimethyl ether, which is an additional advantage. Removal of carbon dioxide from the dimethyl ether product downstream the synthesis reactor can become very costly.

Three basic processes for disposing off carbon dioxide are known. In the first process dimethyl ether is synthesized according to reactions (1) to (3) above. A mixed effluent stream comprising unreacted synthesis gas together with any carbon dioxide present is then separated from the dimethyl ether product, which also contains some unreacted methanol. The separated synthesis gas and carbon dioxide stream is recycled to the synthesis gas process stream entering the reactor. This process may conveniently be applied in a hydrogen rich synthesis gas having for instance a ratio between hydrogen and carbon monoxide above 5.

In the second known process a mixed effluent stream comprising unreacted synthesis gas together with carbon dioxide is separated from the dimethyl ether product. However, carbon dioxide is then subsequently separated from the synthesis gas. This can be done by washing this stream with for instance a suitable amine compound such as methyl diethanol amine, MDEA. The synthesis gas stream which is free of carbon dioxide is then recycled to the synthesis gas process stream entering the reactor. The carbon dioxide obtained may be employed in other processes for instance in the preparation of synthesis gas from natural gas by autothermal carbon dioxide reforming.

In the third known process only synthesis gas is separated from the dimethyl ether product and carbon dioxide. The dimethyl ether product thus contains both methanol and carbon dioxide. The separated synthesis gas is recycled to the synthesis gas process stream entering the reactor.

Various solvents are known in the prior art for removing carbon dioxide from mixtures with synthesis gas. The choice of solvent is dependent on the ability to dissolve dimethyl ether and carbon dioxide and the ideal solvent should have a high solubility for carbon dioxide and a low volatility.

U.S. Pat. No. 5,908,963 discloses a process for the preparation of dimethyl ether from synthesis gas in which synthesis gas is separated from dimethyl ether product and recycled to the synthesis gas process stream entering the dimethyl ether synthesis loop. The presence of excess methanol in the dimethyl ether product is the focus of the disclosed process and the removal of carbon dioxide is not addressed.

U.S. Pat. No. 6,458,856 discloses a one-step catalytic conversion process for dimethyl ether preparation. After catalytic conversion of synthesis gas to dimethyl ether the effluent from the reactor is separated into a vapour mixture comprising dimethyl ether, carbon dioxide and unconverted synthesis gas. The vapour mixture is scrubbed using a scrubbing solvent to remove dimethyl ether and carbon dioxide from unconverted synthesis gas. The scrubbing solvent comprises a mixture of dimethyl ether and methanol. The unconverted synthesis gas is recycled to the dimethyl reactor.

This reference also discloses prior art in which scrubbing solvents such as methanol, water, methanol/water mixtures, dimethyl ether or ethanol are used.

Dimethyl ether is a good solvent for carbon dioxide but is very volatile, whereas methanol is a poorer solvent for carbon dioxide than dimethyl ether but has the advantage of being less volatile. A process for preparing dimethyl ether from synthesis gas which makes use of a solvent having high solubility for carbon dioxide and simultaneously low volatility is therefore desirable.

SUMMARY OF THE INVENTION

In its general aspect, the invention concerns an improved dimethyl ether synthesis process utilising a chemical carbon dioxide absorption process and optionally a subsequent solid adsorbent process for removal of carbon dioxide being present in the synthesis gas and being formed during reaction of the gas to dimethyl ether.

More specific, the invention is a process for the preparation of dimethyl ether product by catalytic conversion of synthesis gas to dimethyl ether comprising contacting a stream of synthesis gas comprising carbon dioxide in a first dimethyl ether synthesis step with one or more catalysts active in the formation of methanol and the dehydration of methanol to dimethyl ether to form a product mixture comprising the components dimethyl ether, methanol, carbon dioxide and unconverted synthesis gas, washing the product mixture comprising carbon dioxide and unconverted synthesis gas in a scrubbing zone with a liquid solvent being rich in potassium carbonate or amine and thereby selectively absorbing carbon dioxide in the liquid solvent, subjecting the thus treated product mixture to a distillation step to separate methanol and water from dimethyl ether and unconverted synthesis gas stream with reduced carbon dioxide and separating the unconverted synthesis gas from the dimethyl ether product.

Liquid solvents being particularly suitable for use in the invention are selected from aqueous solvent containing potassium carbonate as used in the per se known Benfield™, Vetrocoke™ or Catacarb™ process.

In an embodiment of the invention, the product mixture having been treated in with the liquid solvent is further contacted with solid carbon dioxide adsorbent for the deep removal of remaining carbon dioxide.

Suitable solid adsorbents for the selective removal of carbon dioxide are selected from the group of zeolites and molecular sieves such as 13-X and an activated alumina.

In further an embodiment, unconverted synthesis gas being separated from the dimethyl ether product and being depleted in carbon dioxide is recycled to the dimethyl ether synthesis.

In yet another embodiment of the invention, methanol and water having been separated from the dimethyl ether product are passed to a second dimethyl ether synthesis step for further conversion of methanol to dimethyl ether.

DETAILED DESCRIPTION OF THE INVENTION

Figure 1:
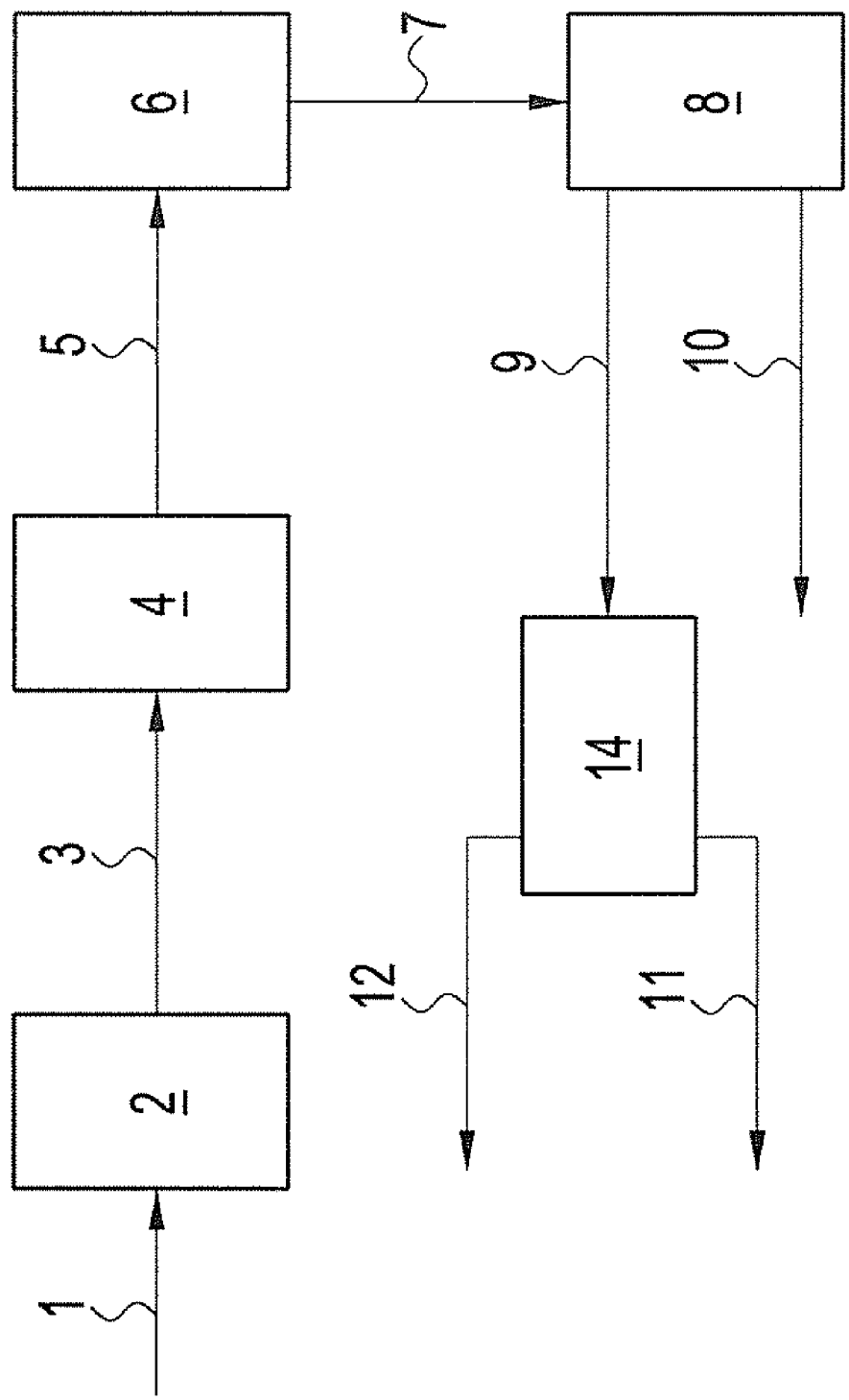
FIG. 1 shows a simplified flow sheet of a specific embodiment of the invention utilising a single-step dimethyl ether synthesis process.

FIG. 1 shows the general process steps in the preparation of dimethyl ether from synthesis gas.

Synthesis gas 1 is sent to DME synthesis reactor 2 for catalytic conversion to methanol and DME according to reactions (1) and (2). The shift reaction also takes place according to reaction (3). The effluent from DME synthesis reactor 2 contains product mixture 3, which comprises a mixture of dimethyl ether, carbon dioxide and unconverted synthesis gas. Product mixture 3 is cooled and sent to absorber unit 4 and being stripped with an aqueous solution containing typically 20 to 40 wt % potassium carbonate for the removal of carbon dioxide. The potassium carbonate process is based on reversible reaction (5).

$$K_2CO_3 + H_2O + CO_2 \Longleftrightarrow 2KHCO_3 + \Delta H \quad (5)$$

By the above stripping operation, the content of carbon dioxide in effluent 5 from the stripping zone is below about 500 ppm by volume. Optionally, if lower levels of carbon dioxide are desired, the effluent 5 may be passed to a fixed bed of a solid adsorbent 6, wherein carbon dioxide is selectively adsorbed in the pore system of the adsorbent to a content in the range of one or less ppm by volume. Suitable solid adsorbents are selected from the group of molecular sieves as mentioned hereinbefore. The adsorbent is preferably arranged in at least two beds being operated in parallel (not shown), so that on bed is operated in adsorption mode, when the spent adsorbent in the other bed is regenerated. From adsorbent 6 an effluent 7 is withdrawn being much depleted in carbon dioxide. Dimethyl ether, methanol and water contained in effluent 7 are separated in distillation column 8 by conventional means into a top product 9 containing mainly dimethyl ether and carbon dioxide depleted synthesis gas. At the bottom of column 8 a liquid bottom product 10 is withdrawn consisting of methanol and water. Methanol in bottom product 10 may be recycled to the DME synthesis reactor 2 or it may be reacted to dimethyl ether in a separate reactor by the above reaction (2) and the thus produced dimethyl ether recycled (not shown) to absorber unit 4. The final dimethyl ether product 11 is obtained by condensation of top product 9 in condenser 14 and phase separation of condensed ether 11 from remaining synthesis gas 12. Synthesis gas 12 being depleted in carbon dioxide may advantageously be recycled (not shown) to oxygenate reactor 2.

EXAMPLE

The effect of using the process as described above and shown in FIG. 1 is summarised in Tables 1 to 3 below. Product mixture 3 having been cooled to 130° C. has a composition as shown in Table 1.

TABLE 1

| Component | Nm³/h | Vol. % |
|---|---|---|
| H2 | 37361 | 17.53 |
| H2O | 1255 | 0.59 |
| N2 | 19182 | 9.00 |
| CO | 35582 | 16.69 |
| CO2 | 69187 | 32.46 |
| Methanol | 3173 | 1.49 |
| DME | 47386 | 22.23 |

Having been treated with potassium carbonate wash in absorber unit 4, the effluent 5 is at a temperature of 71° C. when being introduced into solid adsorbent 6. The composition of the effluent 5 is shown in Table 2 and the effluent 7 from adsorbent 6 in Table 3.

TABLE 2

| Component | Nm³/h | Vol. % |
|---|---|---|
| H2 | 37361 | 26.17 |
| H2O | 165 | 0.12 |
| N2 | 19182 | 13.43 |
| CO | 35582 | 24.92 |
| CO2 | 71 | 0.05 |
| Methanol | 3173 | 2.22 |
| DME | 47386 | 33.19 |

TABLE 3

| Component | Nm³/h | Vol. % |
|---|---|---|
| H2 | 37361 | 26.18 |
| H2O | 165 | 0.12 |
| N2 | 19182 | 13.43 |
| CO | 35582 | 24.92 |
| CO2 | 0.14 | 0.0001 |
| Methanol | 3173 | 2.22 |
| DME | 47386 | 33.21 |

The invention claimed is:

1. Process for the preparation of dimethyl ether product by catalytic conversion of synthesis gas to dimethyl ether comprising contacting a stream of synthesis gas comprising carbon dioxide in a dimethyl ether synthesis step in one or more reactors and with one or more catalysts active in the formation of methanol and the dehydration of methanol to dimethyl ether, to form a product mixture comprising the components dimethyl ether, methanol, carbon dioxide and unconverted synthesis gas washing the product mixture comprising carbon dioxide and unconverted synthesis gas in a scrubbing zone with a liquid solvent being rich in potassium carbonate or amine and thereby selectively absorbing carbon dioxide in the liquid solvent, subjecting the thus treated product mixture to a distillation step to separate methanol and water from dimethyl ether and unconverted synthesis gas stream with reduced carbon dioxide content and separating the unconverted synthesis gas from the dimethyl ether product.

2. The process of claim 1 comprising the further step of treating the product mixture leaving the scrubbing zone with a solid carbon dioxide adsorbent upstream the distillation step to further removal of carbon dioxide from the mixture.

3. The process of claim 2, wherein the solid adsorbent is selected from the group consisting of zeolites, molecular sieves, activated aluminas.

4. The process of claim 1, wherein the synthesis gas stream being separated from the dimethyl ether product with a reduced content in carbon dioxide is recycled to the dimethyl ether synthesis.

5. The process of claim 1, wherein the methanol and water having been separated from the dimethyl ether in the distillation step are passed to a second dimethyl ether synthesis step for further conversion of methanol to dimethyl ether.

6. The process of claim 5, wherein a dimethyl ether product stream of the second dimethyl ether synthesis step is recycled to the distillation step to separate water and methanol from dimethyl ether.

* * * * *